(12) United States Patent
Buckman et al.

(10) Patent No.: US 8,556,933 B2
(45) Date of Patent: *Oct. 15, 2013

(54) METHOD AND APPARATUS FOR SOLID ORGAN TISSUE APPROXIMATION

(76) Inventors: Robert F. Buckman, Radnor, PA (US); Jay A. Lenker, Laguna Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/385,170

(22) Filed: Feb. 6, 2012

(65) Prior Publication Data

US 2012/0239084 A1 Sep. 20, 2012

Related U.S. Application Data

(63) Continuation of application No. 11/821,323, filed on Jun. 23, 2007, now Pat. No. 8,114,124, which is a continuation-in-part of application No. 10/358,735, filed on Feb. 4, 2003, now Pat. No. 7,235,090.

(51) Int. Cl.
*A61B 17/08* (2006.01)

(52) U.S. Cl.
USPC .............................. 606/213; 606/215; 606/217

(58) Field of Classification Search
USPC ................ 411/392, 447–449, 514, 924.1; 606/213, 215, 217, 600–302, 309, 310, 606/320
See application file for complete search history.

(56) References Cited

U.S. PATENT DOCUMENTS

| | | |
|---|---|---|
| 2,485,531 A | 10/1949 | Dzus et al. |
| 3,926,193 A | 12/1975 | Hasson |
| 4,402,445 A | 9/1983 | Green |
| 4,534,350 A | 8/1985 | Golden et al. |
| 4,690,443 A | 9/1987 | Brammall .................. 292/307 R |
| 4,796,612 A | 1/1989 | Reese |
| 4,889,119 A | 12/1989 | Jamolkowski et al. |
| 5,102,276 A | 4/1992 | Gourd ........................... 411/392 |
| 5,268,000 A | 12/1993 | Ottieri et al. |
| 5,292,215 A | 3/1994 | Roberts, III ................... 411/424 |
| 5,486,196 A | 1/1996 | Hirschowitz et al. |
| 5,549,619 A | 8/1996 | Peters et al. |
| 5,759,193 A | 6/1998 | Burbank et al. |
| 5,800,436 A | 9/1998 | Lerch |
| 5,910,144 A | 6/1999 | Hayashi |
| 5,928,267 A | 7/1999 | Bonutti et al. |
| 6,086,305 A | 7/2000 | Lat et al. ........................ 411/487 |
| 6,195,949 B1 | 3/2001 | Schuyler .................... 52/223.13 |
| 6,908,275 B2 | 6/2005 | Nelson et al. ................. 411/487 |
| 7,235,090 B2 * | 6/2007 | Buckman et al. ............. 606/215 |
| 8,114,124 B2 * | 2/2012 | Buckman et al. ............. 606/213 |

* cited by examiner

*Primary Examiner* — Darwin Erezo

(57) ABSTRACT

Surgical bolts are useful for solid visceral wound hemostasis. The devices utilize flexible, variable depth transfixing bolts that penetrate the viscera. These bolts bring the tissue into apposition and hold said tissue in apposition while the wound heals. These bolts, or soft tissue rivets, overcome the limitations of sutures that are currently used for the same purposes. The devices are flexible, bendable, and conformable in their wet or dry state. The bolts include pressure plates that are capable of exerting compressive pressure over broad areas of visceral wounds without causing tearing of the friable parenchyma. The bolts are placed and removed by open surgery or laparoscopic access. The bolts can be placed into tissue where both sides of the bolt are exposed, or they can be placed blindly into tissue where the bolt does not protrude out of the tissue at its distal end.

16 Claims, 12 Drawing Sheets

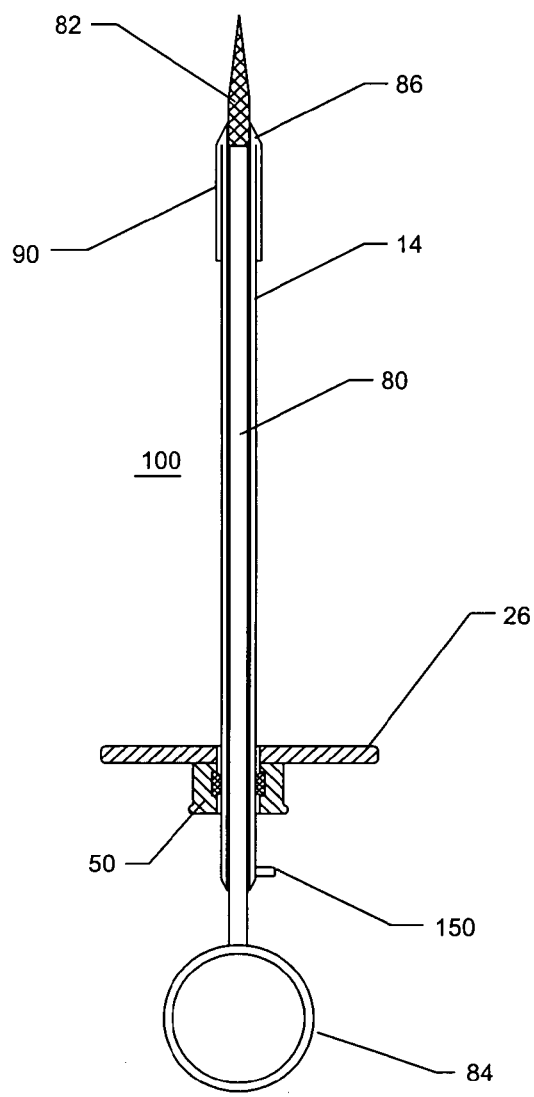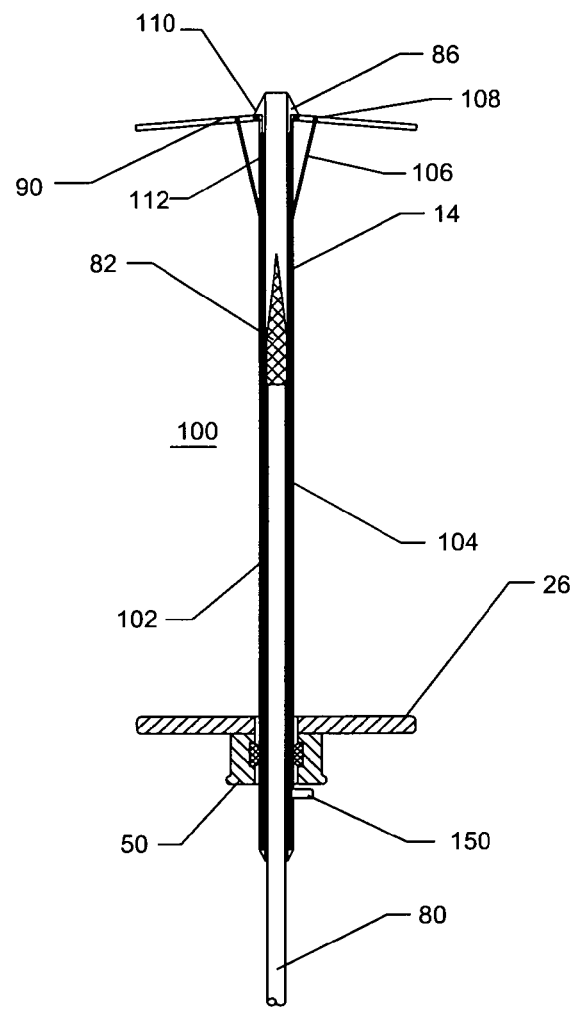
FIG. 9A
FIG. 9B

METHOD AND APPARATUS FOR SOLID ORGAN TISSUE APPROXIMATION

RELATED APPLICATIONS

This application is a continuation of U.S. patent application Ser. No. 11/821,323, filed Jun. 23, 2007 now U.S. Pat. No. 8,114,124, which is a continuation-in-part of, and claims priority benefit from, U.S. patent application Ser. No. 10/358,735 filed Feb. 4, 2003, now U.S. Pat. No. 7,235,090, entitled "Method and Apparatus for Solid Organ Tissue Approximation", the entire contents of which are hereby incorporated herein by reference.

FIELD OF THE INVENTION

The field of this invention relates to devices and methods for trauma and general surgery, combat medicine, and emergency medical services.

BACKGROUND OF THE INVENTION

As recently as the early 1990s, surgical operations for trauma were directed at the anatomic repair of all injuries at time of the initial operation. It was observed during these exercises that many patients became hypothermic, acidotic, and coagulopathic. Patients showing these three signs often died. Death often occurred in the operating room due to exsanguination, or postoperatively, due to the complications of prolonged shock and massive transfusion to replace blood lost as a result of the trauma.

One of the most notable developments in the recent evolution of surgery has been the reintroduction of the concept of staged laparotomy to overcome the deficiencies of the repair all-at-once approach. This new strategy of staged laparotomy employing new tactics that have been termed damage control is now used in 10% to 20% of all trauma laparotomies.

This strategy opens the way for a variety of new devices and methods for control of hemorrhage from solid organs or viscera. Although there are procedures for controlling these injuries, none of these procedures utilize optimal devices or tactics in their execution. Each area offers technological opportunities to improve the devices and procedures for applying those devices.

Sources of hemorrhage within the abdomen that are most difficult to manage include major stellate fractures in the thick, solid, parenchymal organs, especially the liver. Such injuries may involve more than one hepatic lobe, involve massive hemorrhage, and may be caused by severe blunt or penetrating trauma. While the control of most liver hemorrhage is simple, these very severe anatomic wounds are difficult to manage and have a high mortality, sometimes exceeding 80%. Standard approaches to control of these wounds involve packing with gauze or omentum, if available, and deep liver sutures. Each of these techniques has serious limitations and often fails. A major technical problem has to do with the depth to which the sutures can be placed within the liver. The limitation of liver sutures to coapt tissue edges or tamponade deep parenchymal wounds is clear for several reasons. Sutures may be attached to or come pre-mounted to needles of limited size and curvature making deep placement difficult or impossible. The sutures tend to tear through the friable parenchyma. Another problem with sutures is that since they need to be tied off to themselves or other sutures, they form a circular configuration around certain tissues and may strangulate the tissues within that circle. This strangulation causes reduced blood flow and potentially damaging ischemia for those tissues. In addition, the suture does not distribute its force adequately to compress tissues outside of a very narrow plane described by the circle of the suture path. Another key problem with the current treatment is the time taken to achieve suture hemostasis. Massive bleeding must be stopped quickly or the patient will exsanguinate and die. Placement of sutures is a time consuming process given the tools available today, the friable nature of parenchymal tissue, and the undesirability of intra-hepatic gauze packing.

The size and curvature of currently marketed needles is pre-set by the manufacturer. Current needles are not long or big enough to transfix major liver lacerations. Even if the needle was large, the suture method of repair causes inadequate force distribution to create hemostasis and resist progressive wound tearing.

New devices, procedures and methods are needed to support the strategy of damage control in patients who have experienced massive visceral injury. Such devices and procedures are particularly important in the emergency, military, and trauma care setting. These new devices, specifically parenchymal bolts, rely on the principles of broad force distribution on the tissue, pressure tamponade, ease of placement, ease of locking in place with the pressure pads, the ability to adjust tension to optimize tissue compression, and the lack of progressive tearing of the friable wound due to the high shear caused by the suture.

SUMMARY OF THE INVENTIONS

This invention relates to an improved haemostatic tissue apposition device for use in trauma care. The present invention is a transfixing trans-parenchymal bolt. Key features of the bolt include column strength, adjustable depth of penetration, flexibility, tissue non-reactivity, quick and simple application, and adjustment of the pressure plates. The trans-parenchymal bolt uses pressure plates that are affixed to the ends of the bolt to distribute the pressure over a wide area of tissue and compress the tissue. Key features of the pressure plates include one-way ratcheting with quick release or a friction lock, ability to quickly and cleanly remove the pressure plate, and the ability to adjust the pressure plate to ensure optimum tissue apposition and compression. The trans-parenchymal bolt generates pressure tamponade to provide for wound hemostasis. The pressure plates are atraumatic structures such as tabs, leafs, solids, meshes, or other structures that distribute force over a wide area of tissue. By contrast, traumatic structures include pointed projections or small thin wires or whiskers that could rip through parenchymal, or other, tissue. The trans-parenchymal bolt may be placed through an open surgical access site or through a laparoscopic access and manipulation system. The trans-parenchymal bolt, or bolt, can act as, perform the function of, or be equivalent to a soft-tissue rivet. The bolt can also be placed blindly into tissue wherein the distal end of the bolt expands to form a pressure plate thus eliminating the need to access the distal end of the bolt to apply the pressure plate. In this embodiment, the distal pressure plate is activated or expanded by control energy or force applied at the proximal end of the bolt, said control energy being transmitted along the length of the bolt by a linkage, coupling, electronic cabling, or the like. The control energy, or force, then expands the distal pressure plate. Release, or re-collapse, of the distal pressure plate can also be accomplished using the same mechanism at the proximal end of the bolt. The distal and proximal pressure plates are not sharp but are blunted and atraumatic and apply distributed pressure to the tissue.

Once the bolt has been placed, it remains in place either temporarily or permanently. Temporary placement necessitates removal of the bolt. The bolt may be made from materials that permit long-term implantation or it may be fabricated from resorbable materials that obviate the need to remove the bolt in a subsequent surgical procedure. Both the bolt and the pressure plates are fabricated from materials with smooth outer surfaces that do not encourage tissue or clot ingrowth. The bolts and pressure plates are radiopaque and can be visualized on fluoroscopy or X-ray. Thus, the bolts and pressure plates may be removed with minimal re-bleeding.

The current medical practice of utilizing sutures is not an optimized solution to open visceral wound repair. Sutures were not designed for use in parenchymal tissue. The present invention distinguishes over the current medical practice because the present invention is tailored to the needs of open visceral wound repair. The parenchymal bolts are stiff enough to serve as their own needles, trocars, or stylets. They may be flexed or permanently deformed to achieve the desired tissue compression. They are suited for either open surgical implantation and removal, or they are suited for laparoscopic placement and removal using specialized access, grasping and delivery instruments. When the trans-parenchymal bolts of the present invention are removed from the patient, re-bleeding does not occur because there is minimal penetration of the wound tissues or clot into the interstices of the bolt and pressure plate.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 9A illustrates a side cross-sectional view of a parenchymal bolt comprising a distal pressure plate that is integral to the bolt and opens to apply pressure to tissue once the bolt has been placed through tissue or released, according to an embodiment of the invention;

FIG. 9B illustrates a side cross-sectional view of a parenchymal bolt comprising a distal pressure plate that is integral to the bolt and has opened following partial withdrawal of the sharp trocar, according to an embodiment of the invention.

DETAILED DESCRIPTION OF THE INVENTION

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

Figure 1A:
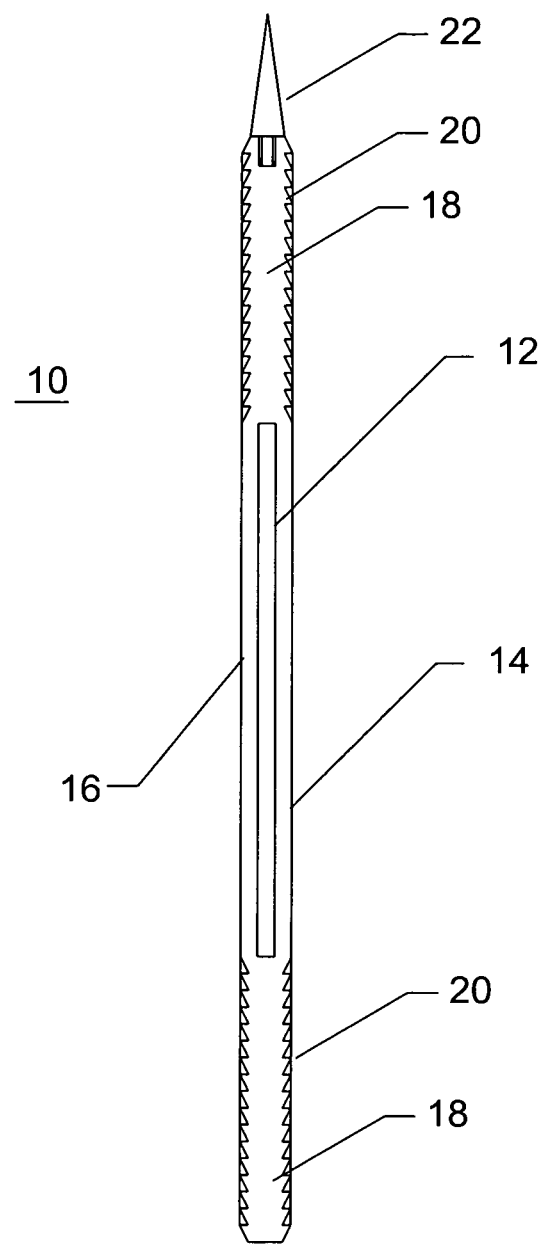
FIG. 1A illustrates a longitudinal cross-sectional view of the parenchymal bolt, according to an embodiment of the invention.

FIG. 1A illustrates a longitudinal cross-sectional view of a parenchymal bolt 10 of the present invention. The parenchymal bolt 10 comprises an inner core 12, an outer coating 14, a central region 16, a plurality of ends 18, and a plurality of serrations 20 on one or both ends 18. The parenchymal bolt 10 further comprises an optional pointed tip or trocar 22.

Referring to FIG. 1A, inner core 12 of the parenchymal bolt 10 is coaxially affixed to interior of the outer coating 14. The central connecting region 16 is disposed between the ends 18. One or more of the ends 18 of the parenchymal bolt 10 comprise a plurality of serrations 20 disposed longitudinally, along at least one side of one or more ends 18. The optional pointed tip or trocar 22 is removably affixed coaxially to one or more of the ends 18.

Referring to FIG. 1A, the inner core 12 of the parenchymal bolt 10 provides column strength and the ability to be malleable or elastomeric, depending on the patient requirements. The preferred configuration of the inner core 12 is that it is malleable and located in the central region 16 only. The ends 18 are, preferably, elastomeric and do not have the malleable inner core 12 disposed therethrough. Another important advantage of having only polymeric material comprise the ends 18 is that the ends can be cut off or trimmed to size once the parenchymal bolt 10 is fully installed or placed in the patient. Column strength is important so that tension may be transmitted through the parenchymal bolt 10, even when the parenchymal bolt 10 has been bent into an arc. Column strength also permits the parenchymal bolt 10 to be forced through tissue much the same as a suture needle would be forced through tissue. Malleability is important so that the parenchymal bolt 10 can be bent into the correct curvature needed for optimum coaptation of the tissue being repaired.

The inner core 12 is fabricated from materials such as stainless steel, cobalt-nickel alloys, nitinol, tantalum, titanium, polylactic acid, polyglycolic acid, platinum, and the like. The inner core 12 is preferably radiopaque and visible under fluoroscopy or X-Ray. It is important that the parenchymal bolt 10 be radiopaque.

The outer coating 14 is fabricated from the same materials as are used to fabricate the inner core 12. The outer coating 14 may be the same physical structure as the inner core 12. Preferably, the outer coating 14 is smooth and does not allow tissue ingrowth. The outer coating 14 may be fabricated from polymers such as, but not limited to, polypropylene, polyethylene, polyester, polyurethane, polylactic acid, polyglycolic acid, polyimide or copolymers of these materials. In a preferred embodiment, the bolt 10 comprises radiopaque markers. The markers are fabricated from tantalum, gold, platinum, stainless steel, titanium, nitinol, cobalt nickel alloys and the like. The markers show the extents of the outer coating 14. The addition of barium, barium compounds, or the like in concentrations of up to about 40% in the polymer provides for radiopacity.

One or more of the ends 18 comprise an optional sharpened or tapered tip 22 to pierce tissue with minimal resistance. The optional pointed tip or trocar 22 facilitates passage of the parenchymal bolt 10 through tissue. The pointed tip or trocar 22 may be removed to minimize further tissue damage while the parenchymal bolt 10 is in place. In a preferred embodiment, the pointed tip or trocar 22 is removably attached to the ends 18 by a male threaded stub that is mated into a female threaded adapter on the end 18. A bayonet mount is another suitable method of attaching the pointed tip or trocar 22 to the end 18. In another embodiment, the pointed tip or trocar 22 may also be longitudinally disposed through the entire core of the parenchymal bolt 10 and is removed by simply withdrawing the trocar 22 from the parenchymal bolt 10. The removable sharp tip 22, in a further embodiment, is retractable within the end 18 of the parenchymal bolt 10. Retraction of the sharp tip 22 is either automatic or manually activated.

One or more of the ends 18 comprise the plurality of serrations 20 that permit locking with devices that are attached to the parenchymal bolt 10 in a later process. The serrations 20 are, preferably, triangular in shape and project outward from the longitudinal axis of ends 18. In the preferred embodiment, the serrations 20 comprise triangular projections. One side of the triangular projection is perpendicular to the longitudinal axis of the end 18. The perpendicular side of the triangle may also be undercut. Another side is tapered away from the end 18 and forms a ramp moving inward from the end 18 toward the center 16 of the parenchymal bolt 10.

Figure 1B:
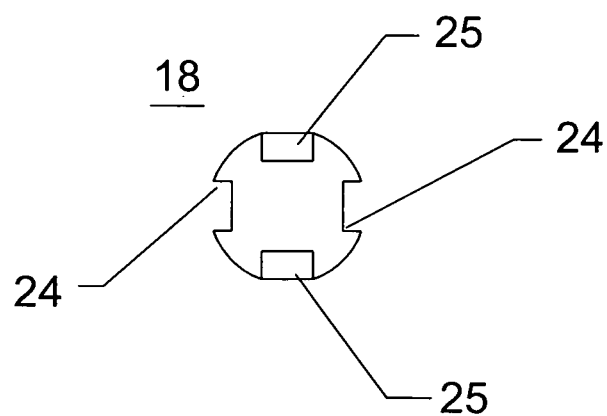
FIG. 1B illustrates a lateral cross-sectional view of the parenchymal bolt near one of the ends, according to an embodiment of the invention.

FIG. 1B illustrates a cross-section of the parenchymal bolt 10 taken near one of the ends 18. The cross-sectional view of the end 18 further comprises one or more optional tracking grooves 24 and one or more optional longitudinal ratchet slots 25.

Referring to FIG. 1B, the tracking groove 24 is a slot and is disposed longitudinally along the length of ends 18. The longitudinal ratchet slot 25 is disposed longitudinally along the length of ends 18.

Referring to FIGS. 1A and 1B, the serrations 20 are disposed within the ratchet slot 25. The ratchet slot 25 holds and hides the serrations from the tissue as the parenchymal bolt 10 is advanced through the tissue to minimize trauma. The tracking groove 24 is used to provide alignment for parts that will be mated to the parenchymal bolt 10. By having two sets of tracking grooves 24, bilateral symmetry is achieved and parts can be mated in two orientations, rather than just one, thus facilitating the mating process. One ratchet slot 25 is required for each set of serrations and two ratchet slots 25 permit orientation of mating parts in more than one orientation. When more than one ratchet slot 25 and tracking groove 24 are used on each end, the second slot 25 or groove 24 is disposed 180 degrees around the end 18 circumference from the first slot 25 or groove 24.

Figure 1C:
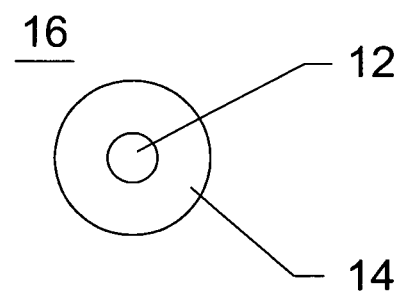
FIG. 1C illustrates a lateral cross-sectional view of the parenchymal bolt near the center, according to an embodiment of the invention.

FIG. 1C illustrates a cross-section of the central region 16 of the parenchymal bolt 10. The central region 16 comprises the core 12 and the outer coating 14. The outer coating 14 is disposed coaxially around the core 12. The optional tracking grooves 25 are not shown in this cross-section.

Figure 2A:
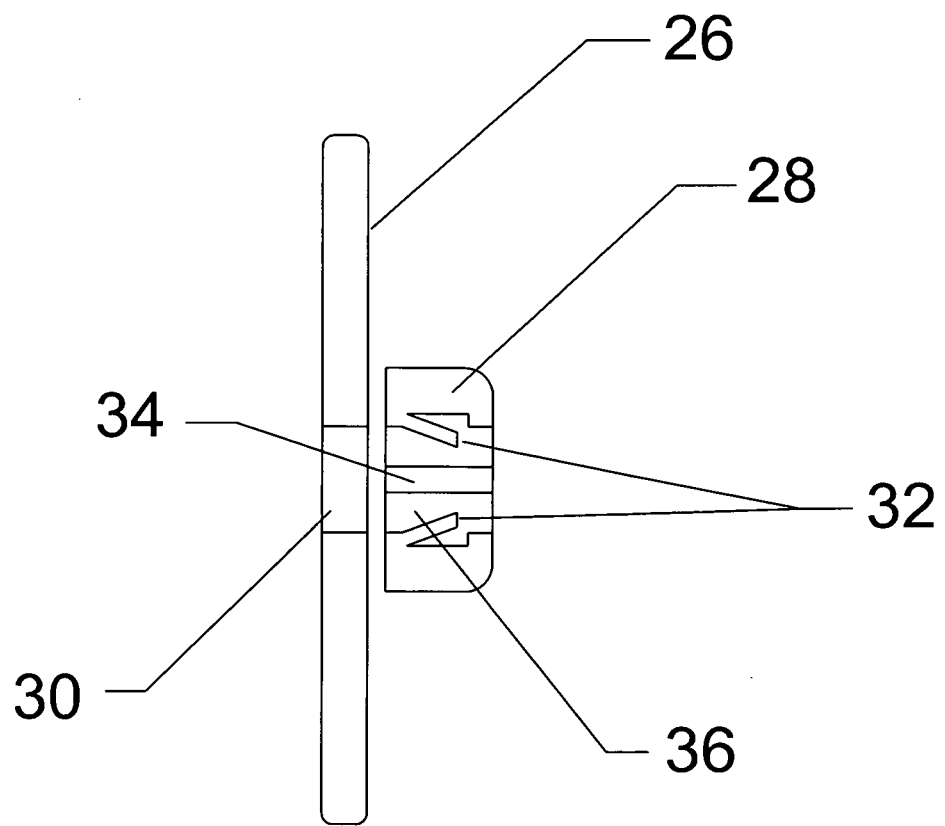
FIG. 2A illustrates a side view of the pressure plate and locking nut in cross-section, according to an embodiment of the invention.

FIG. 2A illustrates a cross-sectional view of a pressure plate 26 and a ratcheting lock 28. The pressure plate 26 further comprises one or more pass through holes 30. The ratcheting lock 28 further comprises a plurality of locking tabs 32, a tracking protrusion 34, and a central hole 36.

The ratcheting lock 28 is disposed coaxially with the pass through hole 30 on the pressure plate 26. The ratcheting lock 28 is either affixed to the pressure plate 26, is integral to said pressure plate 26, or is mounted separately outside the pass through hole 30 of said pressure plate 26. The locking tabs 32 are flexibly affixed to the ratcheting lock 28 and project inward with a vertical edge toward the pressure plate 26 and a ramped edge sloping away from the pressure plate 26. The tracking protrusion 34 is one or more small projections into the central hole 36 of the ratcheting lock 28.

The pressure plate 26 may have a single pass through hole 30 or it may have the plurality of pass through holes 30. With the plurality of pass through holes 30, one pressure plate 26 can be used with multiple parenchymal bolts 10.

Referring to FIGS. 1A, 1B, and 2A, the end 18 is configured to mate with the ratcheting lock 28 and the pressure plate 26. When the ratcheting lock 28 is advanced over one of the ends 18, through the central hole 36, the flexible locking tab 32 on the ratcheting lock 28 is bent aside by the ramp formed on the outside of serrations 20 and allows advancement of the ratcheting lock 28 to continue. Pulling backward on the ratcheting lock 28 or pressure plate 26 causes the vertical edge of the locking tab 32 to dig into the perpendicular sides described by the inner edges of the serrations 20 on the ends 18 so the ratcheting lock 28 will not slip backwards. The tracking protrusion 34 slideably mates with the alignment groove 24 on the end 18 to prevent the locking tabs 32 from becoming misaligned with the serrations 20 and inadvertently disengaging.

Figure 2B:
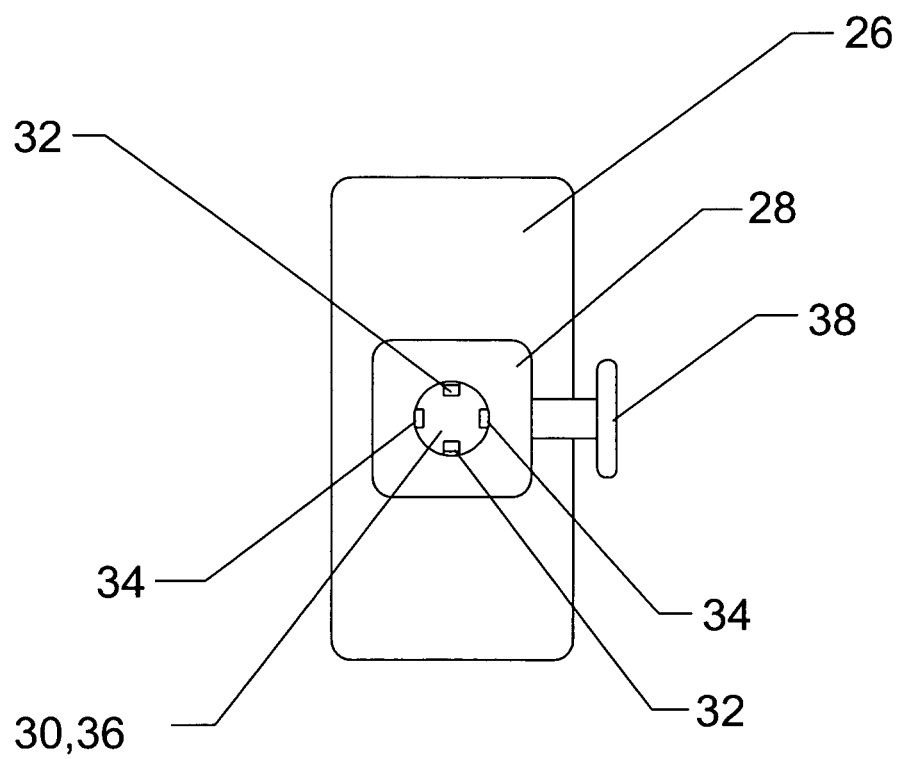
FIG. 2B illustrates an end view of the pressure plate and locking nut also showing the lock release, according to an embodiment of the invention.

FIG. 2B illustrates an end view of the pressure plate 26 and the ratcheting lock 28. As seen in this view, the ratcheting lock 28 further comprises a lock release 38.

Referring to FIGS. 2A and 2B, the locking tabs 32 project inward toward the center of the central hole 36 in the ratcheting lock 28. The lock release 38 is activated by manual pressure or by a laparoscopic instrument to bend back and release the locking tab 32 from the serrations 20 so that the ratcheting lock 28 and pressure plate 26 may be removed from the end 18. The lock release 38 allows for quick release of the ratcheting lock 28 and pressure plate 26. In another embodiment, the lock release 38 retracts the tracking protrusions 34 so that the ratcheting lock 28 can be rotated to disengage the locking tabs 32 from the serrations 20 and enable removal of the ratcheting lock 28 and the pressure plate 26 from the parenchymal bolt 10.

The pressure plate 26, the ratcheting lock 28 and the lock release 38 are fabricated from the same materials as are used in fabrication of the parenchymal bolt 10. All parts are designed with smooth outer surfaces to minimize the opportunity for tissue or thrombus ingrowth. The pressure plate 26 is stiff enough to distribute pressure to gently hold the tissue together while it heals. In a preferred embodiment, the pressure plate 26 and the ratcheting lock 28 are radiopaque. Materials such as barium, barium compounds, or radiopaque metals or the like, comprise at least part of the pressure plate 26 or lock 28.

Referring to FIGS. 1A, 1B, 1C, 2A and 2B, the length of the parenchymal bolt 10 ranges from 0.5 cm to 500 cm depending on the tissue being compressed. More preferably, the length of the parenchymal bolt 10 ranges from 2 cm to 50 cm. The diameter of the parenchymal bolt 10 varies and is in proportion to the length of the bolt 10. Diameter ranges of between 0.5 mm and 10 mm are appropriate for the parenchymal bolt 10. The pressure plate 26 is sized to the organ being compressed. The pressure plate 26 has roughly rectangular dimensions ranging from a minimum of 0.5 cm to a maximum of 100 cm. The preferred range of sizes for the pressure plate 26 is 1 cm to 20 cm. The pressure plate 26 thickness ranges from 0.5 mm to 30 mm.

Figure 3:
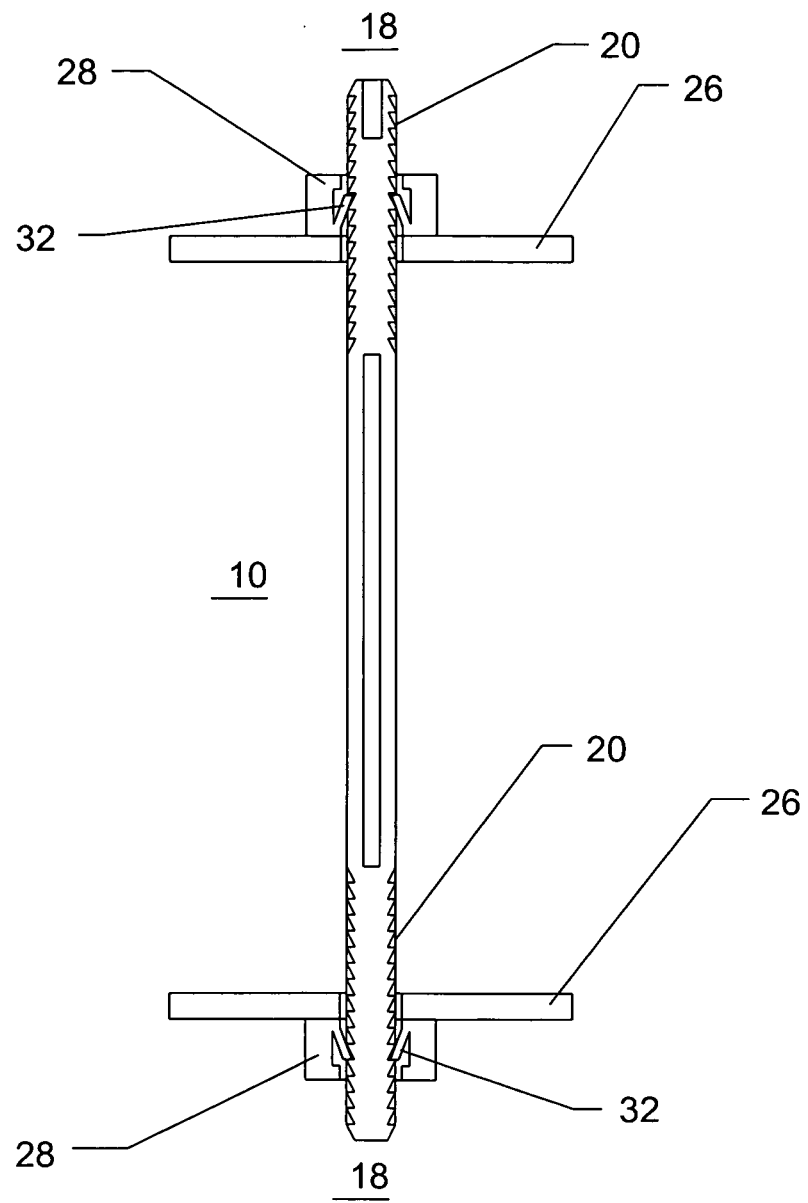
FIG. 3 illustrates a longitudinal cross-sectional view of the parenchymal bolt, two pressure plates and two locking nuts, according to an embodiment of the invention.

FIG. 3 illustrates a longitudinal cross-sectional view of the parenchymal bolt 10 with two pressure plates 26 and two ratcheting locks 28. The pointed tip or trocar 22 has been removed in this view. The pressure plates 26 and ratcheting locks 28 have been pushed over the ends 18 of the parenchymal bolt so that the locking tabs 32 have engaged the serrations 20.

Figure 4:
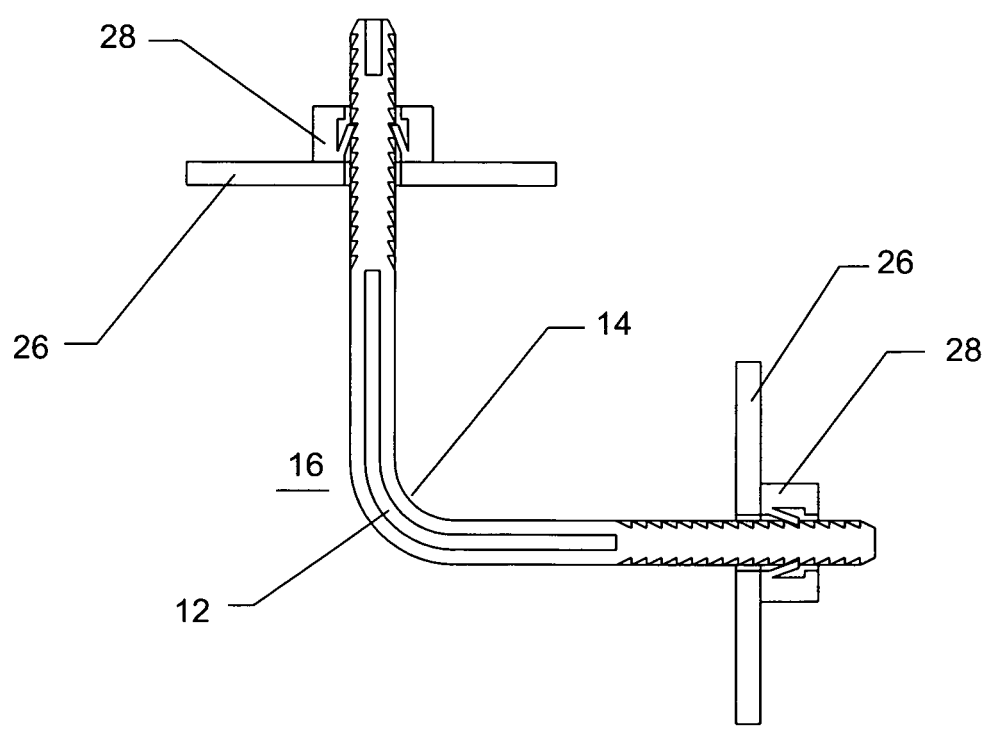
FIG. 4 illustrates a longitudinal cross-sectional view of the parenchymal bolt, two pressure plates and two locking nuts wherein the parenchymal bolt has been malleably deformed into a right angle bend, according to an embodiment of the invention.

FIG. 4 illustrates a longitudinal cross-sectional view of the parenchymal bolt 10 with two pressure plates 26 and two ratcheting locks 28. The parenchymal bolt 10 has been malleably deformed in its central region 16 and maintains that shape because the core 12 has sufficient strength to overcome the elastic forces generated by the outer covering 14.

Figure 5A:
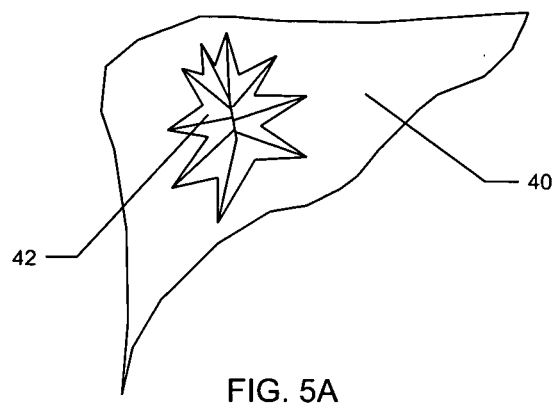
FIG. 5A illustrates a typical wound to the liver, according to an embodiment of the invention.

FIG. 5A illustrates a wound 42 in a liver tissue 40. The liver is a prime example of parenchymal tissue that often receives damage during abdominal trauma. Note that the parenchymal tissue of the liver 40 is friable and unable to sustain high stresses without fracturing or tearing.

Figure 5B:
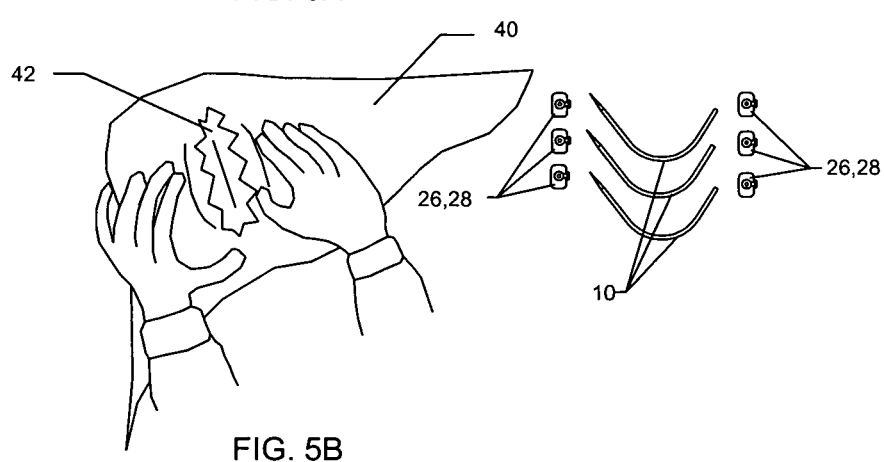
FIG. 5B illustrates preparations for open access liver wound hemostasis using three parenchymal bolts, six pressure plates and six ratcheting locks, according to an embodiment of the invention.

FIG. 5B illustrates open surgical preparation for repair of the liver wound 42 according to the methods of the present invention. In this case, three parenchymal bolts 10, six pressure plates 26 and six ratcheting locks 28 are prepared for the procedure while the liver 40 apposition is accomplished with manual pressure.

Figure 5C:
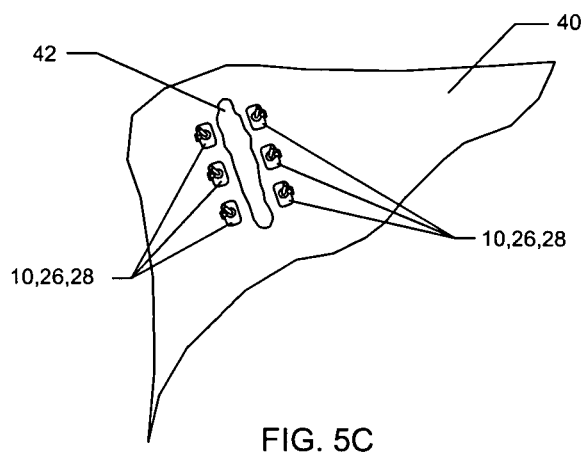
FIG. 5C illustrates the wound to the liver following temporary repair with three parenchymal bolts, six pressure plates, and six ratcheting locks, according to an embodiment of the invention.

FIG. 5C illustrates completion of the repair of the wound 42 to the liver 40 using the parenchymal bolts 10, pressure plates 26 and ratcheting locks 28. The ratcheting locks 28 are tightened sufficiently to hold the pressure plates 26 firmly against the tissue causing complete wound 42 closure and hemostasis.

Figure 6A:
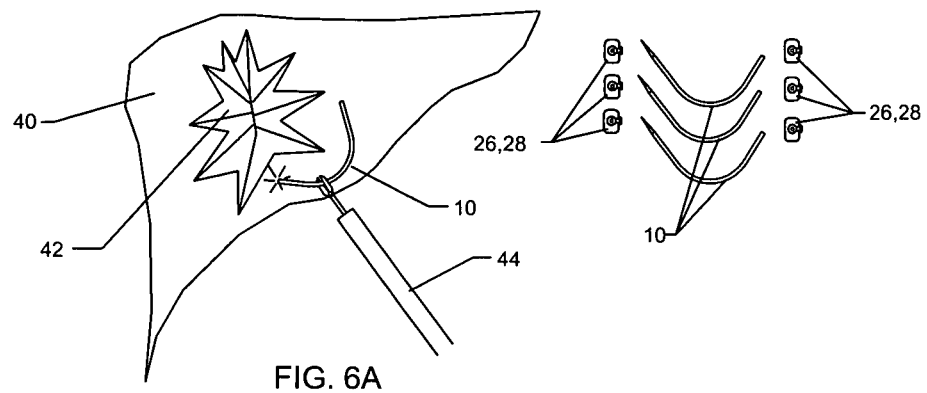
FIG. 6A illustrates a wound to the liver being repaired through laparoscopic access by application of a parenchymal bolt, according to an embodiment of the invention.

FIG. 6A illustrates the wound 42 to the liver 40 with the parenchymal bolt 10 being applied by a laparoscopic instrument 44. In this embodiment, the laparoscopic instrument 44 is a grasper or set of jaws, placed through an axially elongate hollow structure 48, that may be manipulated by the surgeon from the outside of the patient.

Figure 6B:
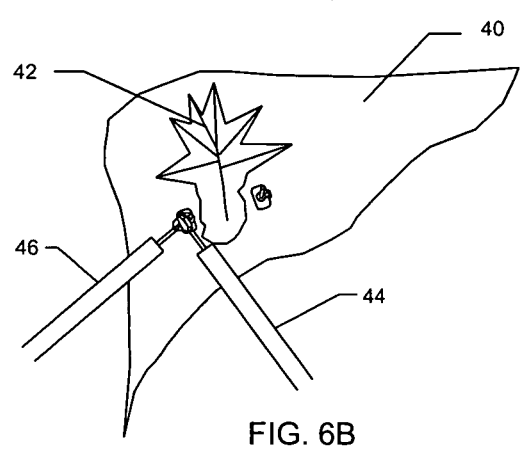
FIG. 6B illustrates application and tightening of a pressure plate and ratcheting lock via laparoscopic instrumentation, according to an embodiment of the invention.

FIG. 6B illustrates the wound 42 to the liver 40 following placement of the first parenchymal bolt 10, two pressure plates 26 and two ratcheting locks 28 using the first laparoscopic instrument 44 and a second laparoscopic instrument 46. Again, the laparoscopic instruments 44 and 46 are placed through an axially elongate hollow structure 48 that provides access to the internal organs of the patient. The laparoscopic grasping device 46 is placed around the ratcheting lock 28 and is used to advance the ratcheting lock 28 and pressure plate 26 inward against the liver tissue 40. The laparoscopic grasping device 44 applies tension to the parenchymal bolt 10 so that the pressure plate 26 and the ratcheting lock 28 move relative to the parenchymal bolt 10. The laparoscopic grasping instruments 44 and 46, which may be similar to very long nosed pliers, may be replaced by a single instrument that performs both functions of stabilizing the parenchymal bolt 10 and advancing the ratcheting lock 28. This type of procedure is generally performed under direct vision through a lens and illuminator placed laparoscopically within the surgical field.

Figure 6C:
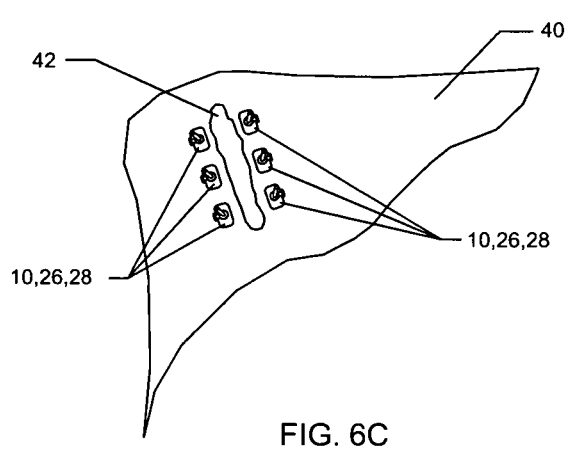
FIG. 6C illustrates the wound to the liver following laparoscopic placement of three parenchymal bolts, six pressure plates, and six ratcheting locks, according to an embodiment of the invention.

FIG. 6C illustrates the wound 42 to the liver 40 following laparoscopic repair with three parenchymal bolts 10, six pressure plates 26 and six ratcheting locks 28.

Figure 7A:
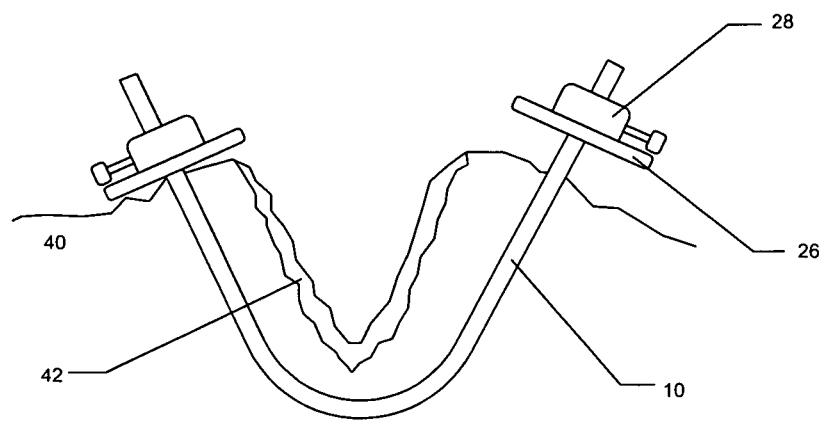
FIG. 7A illustrates a side cross-sectional view of a parenchymal tissue injury with a parenchymal bolt, two pressure plates, and two ratcheting locks prior to tightening, according to an embodiment of the invention.

FIG. 7A illustrates a side cross-sectional view of the wound 42 to parenchymal tissue 40, in this case the liver 40, following initial repair with the parenchymal bolt 10 of the present invention. The repair of the wound 42 comprises placement of the parenchymal bolt 10 followed by placement of two pressure plates 26 and two ratcheting locks 28.

Referring to FIG. 7A, FIG. 1A and FIG. 2A, the pointed tip or trocar 22 has been removed or retracted following full tissue 40 penetration by the parenchymal bolt 10. Two pressure plates 26 have been applied to the ends 18 of the parenchymal bolt 10 to transfix the tissue 40. Two ratcheting locks 28 are in the process of being tightened over the pressure plates 26 and the wound 42 is still open.

Figure 7B:
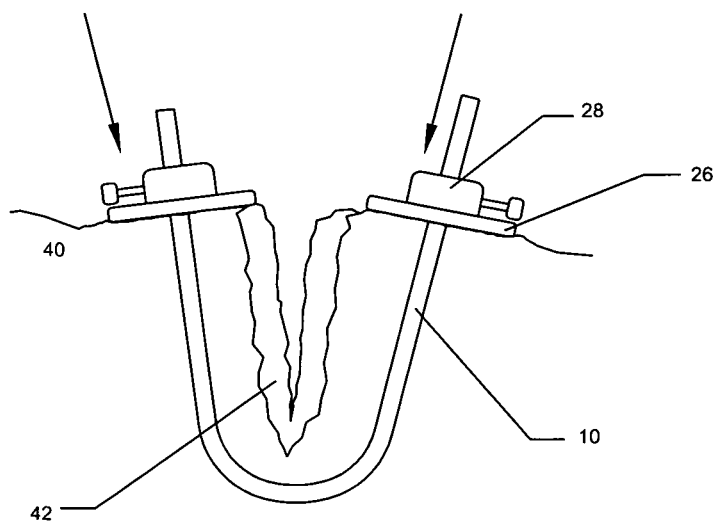
FIG. 7B illustrates a side cross-sectional view of the parenchymal tissue injury during tightening of the ratcheting locks, according to an embodiment of the invention.

FIG. 7B illustrates the wound 42 in the parenchymal tissue 40 at a point where the ratcheting locks are nearly tightened against the tissue 40. The wound 42 has achieved nearly complete closure. Additional inward tightening of the ratcheting locks 28 will compress the pressure plates 26 and achieve full wound 42 closure and hemostasis. The parenchymal bolt 10 flexes to accommodate the change in wound geometry as the ratcheting locks 28 are tightened.

Figure 8:
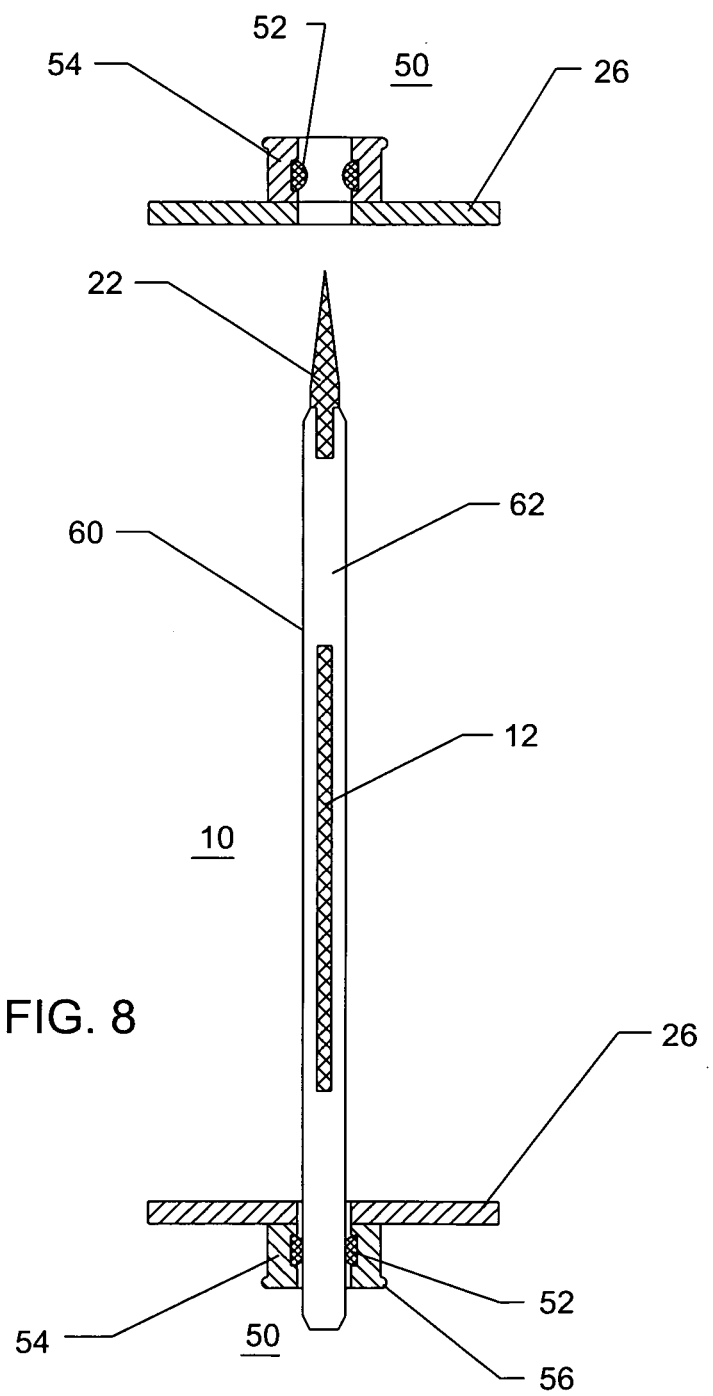
FIG. 8 illustrates a longitudinal cross-sectional view of a parenchymal bolt comprising pressure plates and friction locks, according to an embodiment of the invention.

FIG. 8 illustrates another embodiment of the parenchymal bolt 10, shown in longitudinal cross-section. The parenchymal bolt 10 further comprises an axially elongate shaft 14, a malleable central component 12, a sharpened tip 22, one or more pressure plates 26, and one or more friction locks 50.

The friction lock 50 further comprises a friction generator 52 and a housing 54, which further comprises a grasping bump 56.

The key enhancement to this embodiment of the parenchymal bolt 10 is the friction lock 50. The friction lock 50 may be separate or integral to the pressure plate 26. The friction lock 50 is fabricated from biocompatible polymeric materials such as, but not limited to polyethylene, polypropylene, ABS, PVC, stainless steel, PTFE, titanium, polylactic acid (PLA), polyglycolic acid (PGA), and the like. The PLA or PGA fall under a class of materials that are bioresorbable. These bioresorbable, or resorbable, materials will absorb when implanted in body tissue, over a period of time extending from 1 day to 6 months, preferably in the range of 1 week to 3 months. The formulation of the bioresorbable materials can be modified to adjust the resorption time. Other bioresorbable materials include those fabricated with sugars, collagen, protein, or the like. In the preferred embodiment, the friction lock 50 comprises a friction generator 52, which is a disc with a hole in the center. The hole is smaller in diameter than the outside diameter of the axially elongate shaft 14 of the parenchymal bolt 10. The friction generator 52 comprises elastomeric materials that exert an inward pressure and generate friction against the outside diameter of the axially elongate shaft 14. Such elastomeric materials include, but are not limited to, polyurethane, silicone elastomer, latex rubber, and the like. The friction exerted by the friction lock 50 against the axially elongate shaft 14 is sufficient to resist the force of the tissue resilience once engaged in contact but insufficient to prevent manual movement generated by the surgeon either applying or removing the friction lock 50 from the axially elongate shaft 14. The housing 54 further comprises a grasping surface 56, which is a bump or other feature that allows for easy grasping by the surgeon in a wet or slick environment so that the friction lock 50 may be removed retrograde from the shaft 14 of the parenchymal bolt 10. Other embodiments of the friction lock 50 include those that comprise a jam cleat, an over-center cam, a spring-loaded friction member, and the like. The friction lock 50 preferably does not comprise a release mechanism but in certain configurations, a button or latch to release the friction is required.

FIG. 9A illustrates another embodiment of a parenchymal bolt 100 with a distal pressure plate 90 that is pre-affixed to the bolt 100 prior to use in a patient. The bolt 100 comprises a shaft 14, a trocar 80 further comprising a sharp tip 82 and a trocar handle 84, at least one distal pressure plate 90, a connection region 86, a proximal pressure plate 26, a lock 50, and an actuation lever 100.

The distal pressure plate 90 is configured to fold against the shaft 14 of the bolt 100 when the bolt 100 is being inserted distally through tissue. When the bolt 100 distal end, which carries the distal pressure plate 90, has been advanced through the tissue and is released, the distal pressure plate 90 opens, at least partially due to spring force applied, and can exert pressure on the tissue when pulled proximally. The distal pressure plate 90 is affixed to the shaft 14 by the connection region 86, which can be bendable, can comprise a spring, can comprise an actuator, can comprise releasable locks, or can comprise a hinge. The shaft 14 can be malleable, elastomeric, rigid, pre-bent, shape-memory such that it takes a curved configuration upon exposure to body temperature or a temperature above body temperature generated by Ohmic heating, or the like.

Figure 10:
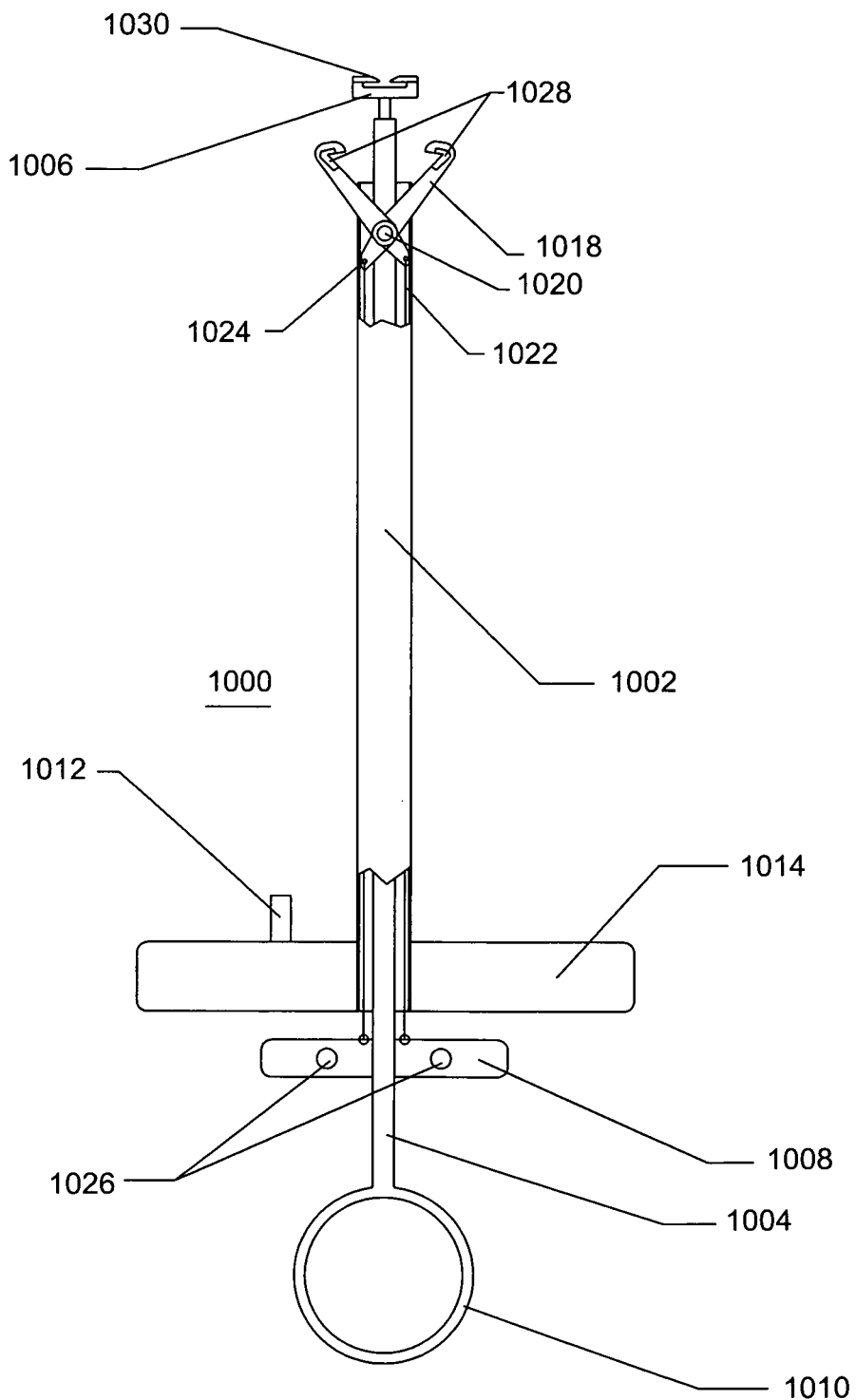
FIG. 10 illustrates a side view of a delivery system for a soft tissue bolt, shown in partial breakaway view, according to an embodiment of the invention.

The distal pressure plate 90, in this embodiment, comprises narrow plates or arms that are separated from the shaft 14 by slots or gaps that allow for expansion of all but the distal region of the pressure plate 90 where it is affixed to the shaft 14 at the connection region 86. In an embodiment, the distal pressure plate 90 can be integral to the shaft 14 and be created by slits or slots in the shaft 14 to form the distal pressure plate 90 elements. The distal pressure plate 90 expandable elements can be held against the side of the shaft 14 by releasable locks, such as those that release or are activated when the tip 82 is withdrawn proximally. The proximal pressure plate 26 and lock 50 are applied in the same way as that of other embodiments of the parenchymal bolt 10. In the preferred embodiment, the proximal pressure plate 26 and lock 50, which can be a friction lock, are pre-positioned on the shaft 14 of the parenchymal bolt 100 or applier and is advanced by the bolt applier, laparoscopic instrument, or manually by the surgeon. In an embodiment the parenchymal bolt 100 can be applied by an instrument such as a bolt applier, laparoscopic instrument, or the like (FIG. 10). This embodiment can be useful when the distal side of the tissue is not easily accessed by the surgical approach and placement of the distal pressure plate 90 would be difficult or impossible. In an embodiment, the sharp pointed tip 82 is retractable or is withdrawn proximally by the user by pulling on the trocar handle 84 affixed to shaft 80 and further affixed to tip 82 once the tissue has been penetrated. The length of the bolt 100 can be adjusted by trimming with the bolt applier or other instrument such as a cutter or pair of scissors. In another embodiment, the length of bolt 100 can also be adjusted using a telescoping, locking configuration in the shaft 14. The telescoping shaft 14 eliminates the need for length trimming. This type of bolt 100 can be used to affix prosthetic devices to soft tissue. The actuator lever 100 is affixed near the proximal end of the shaft 14 and can be moved, either by hand or by an instrument, to force the distal pressure plates 90 outward to engage the tissue.

FIG. 9B illustrates a cross-section of the bolt 100 of FIG. 9A with the distal pressure plate 90 expanded or released. The bolt 100 comprises the shaft 14, the trocar 80, the sharp tip 82, the proximal pressure plate 26, the lock 50, the distal pressure plates 90, the connection region 86, the actuation lever 150, an actuation linkage 102, a linkage lumen 104, one or more lever arms 106, a lever arm hinge 108, an optional distal pressure plate hinge 110, and one or more shaft windows 112.

Referring to FIG. 9B, the distal pressure plate 90, in this embodiment, will appear as a series of radial projections or fingers. Integral or separate leaf springs 86 bias the expandable elements of the distal pressure plate 90 to expand outward. The pointed distal tip 82 and its shaft 80 are slidably movable within the shaft 14. In a preferred embodiment, one or more detents in the shaft 14 mate with protrusions in the shaft 14 to provide a positive positioning index that may be overcome by manual force. In one embodiment, when the distal pressure plate 90 passes beyond tissue, the spring biased pressure plate elements open. In another embodiment, the pressure plate 90 is released when the pointed distal tip 82 and its shaft 80, which are affixed to each other, are withdrawn proximally. The connection region 86 can comprise a spring, an actuator, releasable locks to keep the pressure plates 90 open, or a hinge.

In another embodiment, when the control, or actuation, lever 150 is advanced forward, it forces the actuation linkage 102 to slide distally within the linkage lumen 104 and advance the proximal end of the actuation levers 150. Distal motion of the actuation levers 150 forces the distal pressure plates 90 to open outward around the distal pressure plate hinge 110. Friction in the system or a lever lock 86, which can be releasable and controllable from the proximal end of the bolt 10, or non-releasable, keeps the distal pressure plates 90 open such that they project laterally away from the shaft 14. Backup reinforcements, such as the lever arms 106 prevent the leafs of the distal pressure plate 90 from rotating substantially beyond a plane perpendicular to the axis of the bolt 100.

The distal pressure plates 90 can be configured as wings as shown, or they can be bendable or hinged in the middle such that they open radially or laterally when force is applied at the proximal end of the distal pressure plates 90. In this embodiment, the proximal end of the pressure plate 90, which is constrained not to expand radially is moved distally causing the center of the distal pressure plates 90 to bend, bow, or hinge. This arrangement, similar in configuration to a Moly-bolt, for example, can provide for distal fixation and a pressure-plate effect. Transmission of power from the actuation lumen 104 to the lever arms 106 or distal pressure plates 90, which do not use the lever arm 106, can occur through a window 112 cut in the side of the shaft 14. In yet another embodiment, the distal pressure plates 90 comprise shape memory nitinol that is shape-set during heat-treating to expand radially at body temperature. The nitinol-actuated pressure plates 90 can also be configured to expand radially with the application of electrical energy to the pressure plates 90 causing Ohmic or resistive heating of the nitinol elements above body temperature past a transition temperature, such as the austenite start temperature or austenite finish temperature. The nitinol-actuated pressure plates 90 can be heated using adjunctive heaters such as a nickel chromium wire routed around or near the nitinol actuator. Hysteresis effects can keep the nitinol open even when the bolt 100 or pressure plates 90 are exposed to body temperatures or slightly below. The pressure plates 90 in this embodiment can take the shape of ribbons or wings that are longitudinally disposed along the shaft 14 but bend outward radially or laterally to cause the pressure plate effect. The pressure plates 90 can also take the form of a coil of wire that expands to form a ball or other three-dimensional mesh which can serve the function of a pressure plate.

In an embodiment, the proximal pressure plate 26 can be configured as the mirror image of the distal pressure plate 90. In this embodiment, the proximal pressure plate 26 is actuable, rather than being pre-attached to the shaft 14 with the lock 50. The proximal pressure plate 26 of this embodiment can be a Moly-bolt, a balloon, an expanding wire structure or other configuration similar to that described for the distal pressure plate 90 using the same or similar actuation mechanisms or means. In another embodiment, the bolt 100 can be configured to bend in response to shape memory actuators affixed thereto. The actuation of the shape memory actuators can be performed using electrical energy delivered through a delivery system such as that shown in FIG. 10.

Another aspect of the inventions includes the method of use of the bolt 10. In an embodiment, the bolt 100 is inserted into a patient through the tissue using the fingers or with the aid of an instrument which is axially elongated to provide additional reach into small, narrow spaces unreachable except through undesirable open surgery. The bolt 100 is advanced with its sharp tip 82 exposed through tissue until it has achieved the desired penetration. The sharp tip 82 is then retracted and optionally completely withdrawn from the bolt 100. The distal pressure plates 90 are expanded by actuation from the proximal end, by automatic means such as shape memory expansion, or by proximal pullback or removal of the core, sharp trocar 80. Proximal end pressure plates 26 are either applied, actuated, or expanded using the same or similar means as the distal pressure plates 90. The plates can be adjusted for tightness by causing the proximal pressure plate 26 to slide axially along the shaft 14 and then lock in place with the lock 50. The instrument or hand is then decoupled from the bolt 100 and removed. The bolt 100 is either left permanently, removed by surgery, or left to resorb into the tissue. The bolt 100 can be used to repair damaged parenchymal tissue, or it can be used to repair damaged muscle such as smooth muscle or striated muscle. The use of soft tissue rivets, such as the bolt 100, can be used to speed closure of wounds that result from trauma or surgery. The application of a rapid-fire bolt 100 by means of an installation tool (not shown) can result in placement of multiple bolts 100 in a very short period of time. For example, it is possible to place 5 to 20 bolts 100 in one minute or up to one rivet or bolt 10 every 5 seconds using this type of system.

FIG. 10 illustrates a delivery system 1000 for a soft tissue bolt 100 comprising a main shaft 1002, a pushrod 1004, a distal engagement tab 1006, a grabber control handle 1008, a pushrod control handle 1010, an actuator control lever 1012, a main handle 1014, one or more grasper tabs 1018, a grasper hinge 1020, one or more grasper linkages 1022, one or more grasper linkage connectors 1024, one or more electrical input jack 1026, and one or more grasper electrode 1028.

Referring to FIG. 10, the main handle 1014 is affixed to the main shaft 1002 near the proximal end of the main shaft 1002. The pushrod 1004 is affixed, at or near its proximal end to the pushrod control handle 1010 and at or near its distal end, to the distal engagement tab 1006. The pushrod 1004 is slidably disposed within or near the main shaft 1002, with respect to which it is oriented generally parallel. The grasper tabs 1018 are rotatably affixed about the grasper hinge 1020, which is affixed near the distal end of either the main shaft 1002 or the pushrod 1004. The grasper linkages 1022 are affixed to the grasper tabs 1018 at linkage connectors 1024. Electrical input jack 1026 is affixed to the main handle 1014, the pushrod control handle 1010, or near the proximal end of the main shaft 1002. The grasper electrodes 1028 are affixed to either the grasper tabs 1018 or the distal engagement tab 1006 and are operably connected to the electrical input jacks 1026 by an electrical bus, which can be, in the illustrated embodiment the grasper linkages 1022.

The delivery system 1000 can be used in conjunction with a laparoscopic or thoracoscopic trocar, for example, or through an open surgical port to deliver the soft tissue bolt 100 to a surgical target site. Referring to FIGS. 9A and 9B, the operator grasps the delivery system 1000 by the main handle 1014 with the distal engagement tab 1006 releasably engaging the distal pressure plate 90 expansion control lever 150 on the bolt 100. In another embodiment, the distal graspers can be used to releasably engage the distal pressure plate 90 control lever 150 on the bolt 100. In this embodiment, the distal engagement tab 1006 can be used to withdraw the obturator, shaft 80, or sharpened point of the bolt either partially or fully proximal and out of the bolt 100. In this embodiment, the grasper electrodes 1028 can be used to deliver electrical energy to either bend the bolt 100 or to radially expand the distal pressure plates 90 by shape memory effects using nitinol, or the like in one or both applications. The distal engagement tab 1006 or the grasper tabs 1018 can be configured, in one or more embodiments, to provide cutting action to cut off excess length of the soft tissue rivet, or bolt, 100 during or after the implantation and securing process has been completed. Alternatively, an additional cutter 1030 can be affixed near the distal end of the delivery system 1000 to cut the bolt 100 to length. This is facilitated by removal of any metallic core materials leaving primarily polymeric bolt 100 shaft materials, which can more easily be severed. Control over the cutting action is applied at or near the proximal end of the delivery system 1000 and the control is transmitted to the cutting mechanism by linkages such as the grasper linkages 1022 or the pushrod 1004.

The components of the delivery system 1000 can be fabricated from polymeric materials such as, but not limited to, polycarbonate, polypropylene, polyethylene, PEEK, polyvinyl chloride, acrilonitrile butadiene styrene, polysulfone, or the like. The components can also be fabricated in part, or in whole from metals such as, but not limited to, stainless steel, cobalt nickel alloy, titanium, nickel titanium, tantalum, or the like. The length of the main shaft can range from 2 cm to 50 cm and the diameter of the main shaft can range from 1 mm (3 French) to 25 mm (75 French). The delivery system 1000 can be releasably affixed to the bolt 100 in singles. In another embodiment, multiple bolts 100 can be loaded into the delivery system to permit rapid fire, multiple applications. The delivery system 1000 can control the expansion of the distal, or second, pressure plate. The delivery system 1000 can control retraction of the obturator. The delivery system 1000 can control bending of the bolt 100.

Application of the parenchymal bolt system provides improved speed of solid organ trauma repair and minimizes the chance of tissue tearing or fracture, relative to the use of sutures for said repair. The parenchymal bolt system provides pressure tamponade to the injured tissue to provide for hemostasis and maximize the recovery process while minimizing complications common to suture-based approaches.

The present invention may be embodied in other specific forms without departing from its spirit or essential characteristics. For example, the ratcheting locks could be replaced by simple threaded nuts that engage threads on the parenchymal bolt. The distal pressure plate can comprise one or more radially expandable wings such as are found in a hollow wall anchor, or the distal pressure plate can comprise a fluid-filled balloon such as a non-elastomeric balloon or an elastomeric, Foley-type balloon, or they can be of a radially different shape such as a three-dimensional wire mesh or a solid such as when a hydrogel, constrained within a water permeable membrane, expands due to fluid uptake to swell into a flexible volume. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. An apparatus adapted for achieving closure of soft tissue wounds comprising:
    an axially elongate bolt having a first end and a second end, wherein the bolt comprises a malleable inner core limited to a central region, and an outer polymeric coating disposed coaxially around the core, the outer coating axially extending beyond the central region to the first and second end;
    a first pressure plate attached onto the first end of the bolt, wherein the first pressure plate is fixed at a location axially along the bolt;
    a second pressure plate attached to the second end of the bolt, wherein the second pressure plate is controllably movable axially along the bolt; and
    a lock for longitudinally fixing the second pressure plate along the length of the bolt;
    wherein the first and second pressure plates are atraumatic structures.

2. The apparatus of claim 1 wherein the first pressure plate is radially outwardly expandable and further wherein said radially outward expansion of the first pressure plate is controlled at the first end of the bolt.

3. The apparatus of claim 1 wherein the first pressure plate is radially outwardly expandable when the first pressure plate is embedded within tissue.

4. The apparatus of claim 3 wherein the bolt, the first and second pressure plate, and the lock comprise bioresorbable materials.

5. The apparatus of claim 1 wherein said bolt is malleably bendable in a direction perpendicular to its longitudinal axis.

6. The apparatus of claim 5 wherein said malleable bendability is facilitated by an axially elongate metal support structure.

7. The apparatus of claim 5 wherein said malleable inner core is selected from the group consisting of stainless steel, nitinol, cobalt nickel alloy, titanium, and tantalum.

8. The apparatus of claim 1 wherein the second end of the bolt is exposed outside tissue when the second pressure plate is applied and where the first end of the bolt is not exposed outside tissue when the first pressure plate is radially outwardly expanded.

9. The apparatus of claim 1 wherein said lock comprises a quick release mechanism.

10. The apparatus of claim 1 wherein said bolt further comprises a removable or retractable sharp tip.

11. The apparatus of claim 1 wherein an outer surface of the bolt is smooth and discourages tissue ingrowth.

12. The apparatus of claim 1 wherein the outer surface of the bolt comprises a polymeric material.

13. The apparatus of claim 12 wherein said polymeric material is selected from a group including polyurethane, polyethylene, polypropylene, silicone rubber, polyester polymethylmethacrylate, polyvinyl chloride, or a copolymer including of one of these materials.

14. The apparatus of claim 1 wherein said bolt is radiopaque.

15. The apparatus of claim 1 wherein the first and second pressure plate and lock are radiopaque.

16. The apparatus of claim 1 further comprising an axially elongate support structure fabricated from shape memory material, such that following, during, or prior to implantation, the bolt can be forced to bend laterally to its longitudinal axis due to shape memory transition effects within the shape memory material.

* * * * *